United States Patent [19]

Williamson

[11] 4,182,385
[45] Jan. 8, 1980

[54] VACUUM EVACUATION APPARATUS

[76] Inventor: Ron T. Williamson, Box 19822, Houston, Tex. 77024

[21] Appl. No.: 826,167

[22] Filed: Aug. 19, 1977

Related U.S. Application Data

[63] Continuation-in-part of Ser. No. 655,217, Feb. 4, 1976, abandoned.

[51] Int. Cl.² .............................................. B65B 3/04
[52] U.S. Cl. ...................................... 141/65; 128/276; 141/392
[58] Field of Search ..................... 141/65, 7, 8, 66, 85, 141/93, 392; 138/177, 178; 32/33; 128/276, 277, 278, DIG. 5, 2 F, 348

[56] References Cited

U.S. PATENT DOCUMENTS

| 2,173,637 | 9/1939 | Riedner | 128/276 |
| 3,094,124 | 6/1963 | Birtwell | 128/348 |
| 3,823,750 | 7/1974 | Owen | 141/65 |

Primary Examiner—Houston S. Bell, Jr.

[57] ABSTRACT

A plastic evacuation tube for use with a standard dental and/or surgical vacuum system is disclosed. The tube is formed with an enlarged non-compressible bulb-shaped portion (bulb) intermediate its length. The operational end section of the tube is tapered from the bulb to a smaller diameter flexible tip end and may be provided with spaced apart markings to designate decreasing inner diameters from the bulb to the tip end.

3 Claims, 2 Drawing Figures

U.S. Patent     Jan. 8, 1980     4,182,385
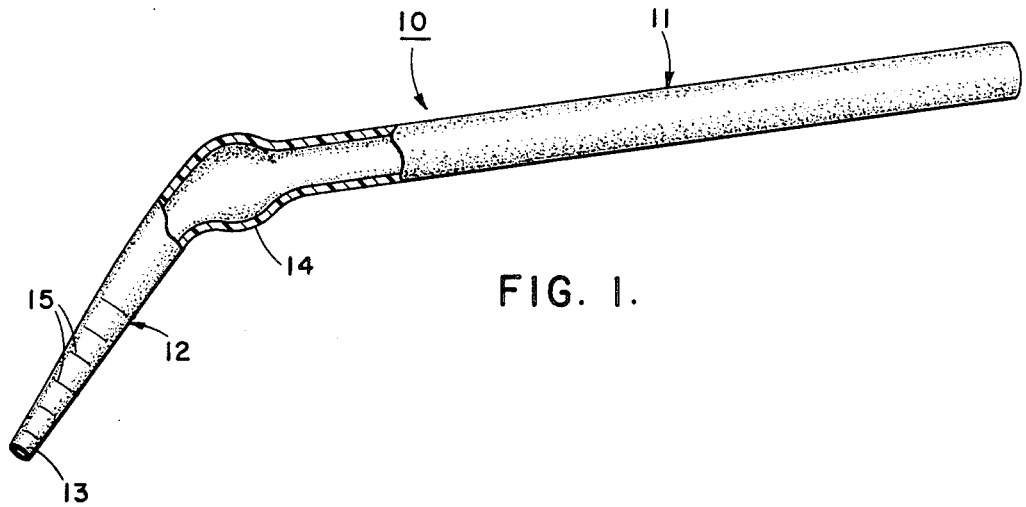
FIG. 1.
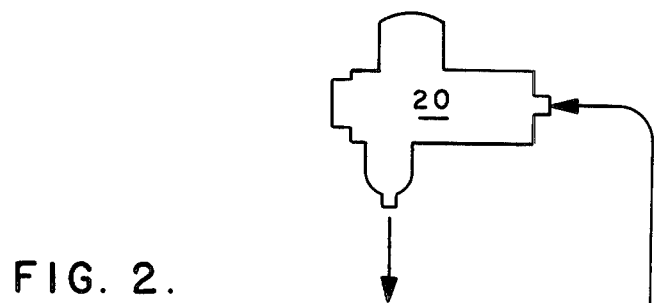
FIG. 2.
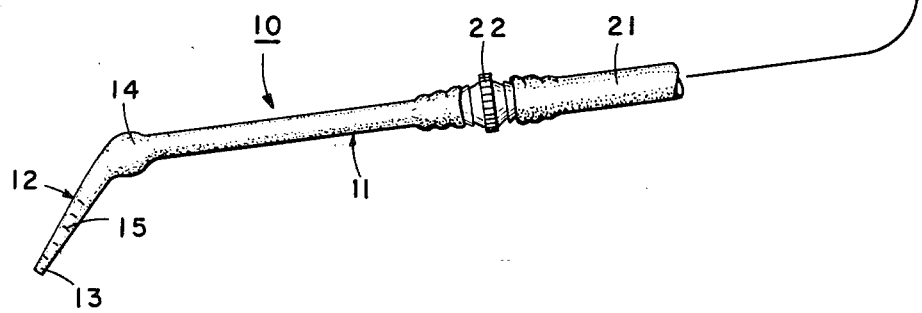

VACUUM EVACUATION APPARATUS

BACKGROUND OF THE INVENTION

This application is a continuation-in-part of application Ser. No. 655,217, filed Feb. 4, 1976, now abandoned.

The present invention concerns evacuation devices designed for connections to and use with standard dental and surgical vacuum systems and, more particularly, a disposable, high evacuation, non-compressible, unitary, clog-proof, easily cleaned suction tube having a flexible tip end. The tube can be made in a variety of sizes and can be designed so that the user will have available a desired orifice size.

SUMMARY OF THE INVENTION

The invention, briefly, comprises a hollow tube having a vacuum section attached to a vacuum system, a flexible operational section having an end tip and an enlarged non-compression type section therebetween. The inner cross-sectional area of the enlarged section increases from its point of connection with each section to form a bulb and the inner wall of the operational section tapers from a larger diameter at the bulb to a smaller diameter at the tip end.

BRIEF DESCRIPTION OF THE DRAWING

FIG. 1 is a partly sectional view of the tube of the invention.

FIG. 2 illustrates the tube of FIG. 1 connected to a vacuum system in accordance with the invention.

DESCRIPTION OF THE PREFERRED EMBODIMENTS

Referring to FIG. 1 there is shown a one-piece hollow tube or tubular member 10 having a (vacuum) substantially inflexible section 11 and a flexible (operational) section 12, provided with an end tip portion 13, designed for insertion into a mouth or other location where a continuous vacuum is to be applied for evacuation of fluids and/or materials during dental or surgical operations. An enlarged non-compression type, substantially inflexible bulb-shaped section 14, located between sections 11 and 12, has an increasing inner cross-sectional area from its point of connection with each end member, as shown, to form a bulb or bubble. Section 12 is tapered to decrease the inner diameter or passageway thereof from the enlarged section 14 to operational end tip 13. Markings 15 provide indications at which the tubular member 10 may be cut off to provide an end tip opening of desired size. Tubular member 10 may be bent along section 12, as shown, to facilitate its manipulation.

As seen in FIG. 2 tube 10 is connected to a standard, commercial vacuum system 20. Vacuum section 11 of tube 10 is shown connected to a vacuum tube 21 by means of a connector 22. Tube 21 connects to the vacuum system intake as indicated by the solid arrowed line.

In operation, enlarged section 14 creates a swirling motion for the fluids and particles of material evacuated through end tip 13. It functions to keep such particles dispersed. The enlarged section also acts as a damper in the event a surge of vacuum occurs from the vacuum system. The vacuum force is normal at end tip 13 and is reduced in bubble 14 in proportion to enlarged cross-sectional areas of the bubble. The lateral suction force component of the vacuum force is reduced from what would be experienced without the bubble at the end tip 13, causing thereby an increase in the axial suction force component along the axis of said operational end section 12 and causing the resultant force vector to move closer to the axial force component to substantially eliminate the undesirable vacuum of materials from sites other than the pin point operative site of the operational end section 13.

The overall length of the tubular member, outside and inside cross-sectional areas (or diameters) of the end sections and the bubble may be varied for desired applications. A typical tube may have an overall length of about four and one-half (4½) inches and the largest cross-sectional area of bubble 14 may be about one and one-third (1⅔) times greater than the cross-sectional area of operational section 11 at the point it joins bubble 14.

Polyethylene is the preferred fabrication material for the tubular member, but other suitable materials may be used instead. The term "vacuum systems" as used herein are meant commercially available systems employed to apply a continuous vacuum. Such systems when portable utilize vacuum motors with and without waste reservoirs. The amount of suction vacuum exerted will vary according to the sizes of the motor, tubing, reservoir and other factors and is chosen by the operator. These systems also vary when permanently installed into the plumbing. They generally contain a central vacuum motor that is capable of creating enough vacuum to operate one or more individual suction lines. The term "non-compression" as used herein means not deformable by compression forces which would be encountered in ordinary normal usage. The term "flexible" as used herein means resilient and capable of being flexed without permanent deformation or rupture. Various modifications may be made in the embodiments of the invention described herein without departing from the spirit of the invention as defined in the appended claims.

Having fully described the advantages, objects, apparatus and operation of my invention, I claim:

1. Vacuum evacuation apparatus comprising:
   a vacuum system;
   a one-piece hollow tubular member having a single vacuum end section attached to said vacuum system, a single flexible operational end section provided with an end tip, and an enlarged non-compression type section between said end sections;
   the inner cross-sectional areas of said operational end section being gradually decreased from said enlarged section to said end tip, to aid in passing material through the remainder of said tubular member, said enlarged section having inner cross sectional areas increasing from its point of connection with each end section to form a bubble, said bubble having a size sufficient to create a swirling motion for fluids and particles of materials evacuated through said operational end section and to act as a damper in the event a surge of vacuum occurs, the vacuum forces at the tip of said operational end section being responsive to the size of said bubble; the lateral suction force component of the vacuum force being reduced at said end tip of said operational section causing thereby an increase in axial suction force component along the axis of said operational end section and causing the resultant force vector to move closer to the axial force component to substantially eliminate the undesirable vacuum of materials from sites other than the pin point operative site of said operational end section.

2. A tubular member as described in claim 1 in which the largest cross-sectional area of said bubble is about one and one-third (1⅓) times greater than the cross-sectional area of said vacuum section.

3. A flexible, hollow tubular member as described in claim 2 in which said tubular member has an angular shape.

* * * * *